United States Patent
Rebinsky

(10) Patent No.: US 9,354,220 B2
(45) Date of Patent: May 31, 2016

(54) ENGINE SYSTEM HAVING FUEL QUALITY SENSOR

(71) Applicant: Caterpillar Inc., Peoria, IL (US)

(72) Inventor: Douglas Alexander Rebinsky, Peoria, IL (US)

(73) Assignee: Caterpillar Inc., Peoria, IL (US)

( * ) Notice: Subject to any disclaimer, the term of this patent is extended or adjusted under 35 U.S.C. 154(b) by 294 days.

(21) Appl. No.: 14/039,504

(22) Filed: Sep. 27, 2013

(65) Prior Publication Data

US 2015/0090222 A1 Apr. 2, 2015

(51) Int. Cl.

| | |
|---|---|
| *G01N 33/22* | (2006.01) |
| *F02D 41/00* | (2006.01) |
| *G01N 25/18* | (2006.01) |
| *G01N 25/20* | (2006.01) |
| *F02D 41/30* | (2006.01) |
| *F02D 19/02* | (2006.01) |
| *F02M 21/02* | (2006.01) |

(52) U.S. Cl.
CPC ............ *G01N 33/225* (2013.01); *F02D 19/029* (2013.01); *F02D 41/0027* (2013.01); *F02D 41/3005* (2013.01); *F02M 21/0215* (2013.01); *G01N 25/18* (2013.01); *G01N 25/20* (2013.01); *F02D 19/024* (2013.01); *F02D 2200/0611* (2013.01); *Y02T 10/32* (2013.01)

(58) Field of Classification Search
CPC ..... G01N 33/225; G01N 25/18; G01N 25/20; F02D 41/0027
USPC ....... 123/525, 526, 527, 27 GE, 381; 702/50; 73/25.03; 374/44, 36, 43, 31, 1
See application file for complete search history.

(56) References Cited

U.S. PATENT DOCUMENTS

| | | | |
|---|---|---|---|
| 4,246,773 A | * | 1/1981 | Haruta ................. G01N 29/024 73/24.01 |
| 4,579,653 A | | 4/1986 | Davis |
| 5,311,447 A | | 5/1994 | Bonne |
| 5,486,107 A | | 1/1996 | Bonne |
| 5,622,053 A | | 4/1997 | Freen |
| 5,778,861 A | | 7/1998 | Diduck |
| 5,932,793 A | | 8/1999 | Dayton et al. |
| 6,209,387 B1 | | 4/2001 | Savidge |
| 6,442,996 B1 | | 9/2002 | Thurston et al. |
| 6,634,214 B1 | | 10/2003 | Thurston et al. |
| 6,688,159 B1 | | 2/2004 | Grunewald |

(Continued)

FOREIGN PATENT DOCUMENTS

| | | |
|---|---|---|
| EP | 1 329 715 | 7/2003 |
| EP | 2 015 056 | 1/2009 |

(Continued)

*Primary Examiner* — Mahmoud Gimie
(74) *Attorney, Agent, or Firm* — Finnegan, Henderson, Farabow, Garrett & Dunner, LLP

(57) ABSTRACT

A fuel quality sensor is provided for use with an engine system. The fuel quality sensor may have a single sensing element configured to sense a thermodynamic property of an unknown mixture of gaseous fuel, and a heating element configured to increase a temperature of the unknown mixture of gaseous fuel at the single sensing element to multiple different temperature levels. The fuel quality sensor may also include a microprocessor configured to calculate a fuel parameter of the unknown mixture of gaseous fuel as a function of only the thermodynamic property sensed at the multiple different temperature levels.

20 Claims, 6 Drawing Sheets

(56) References Cited

U.S. PATENT DOCUMENTS

| | | |
|---|---|---|
| 7,091,509 B2 | 8/2006 | Rahmouni et al. |
| 2006/0283193 A1* | 12/2006 | Nilsson ............... F23K 5/18 |
| | | 60/776 |
| 2007/0089485 A1* | 4/2007 | Antel ............... G01N 25/22 |
| | | 73/25.01 |
| 2007/0163542 A1 | 7/2007 | Kettle et al. |
| 2009/0013759 A1* | 1/2009 | Knobloch ......... G01N 33/225 |
| | | 73/25.05 |
| 2009/0107441 A1 | 4/2009 | Husak et al. |
| 2010/0186482 A1* | 7/2010 | Bierl ............... F02D 41/0045 |
| | | 73/24.06 |
| 2012/0287962 A1 | 11/2012 | Ooishi |
| 2014/0238032 A1* | 8/2014 | Fitzgerald ............ F02C 9/26 |
| | | 60/772 |

FOREIGN PATENT DOCUMENTS

| | | |
|---|---|---|
| EP | 2 372 359 | 10/2011 |
| EP | 2 574 918 | 4/2013 |
| ES | 2 284 296 | 11/2007 |

\* cited by examiner

ENGINE SYSTEM HAVING FUEL QUALITY SENSOR

TECHNICAL FIELD

The present disclosure relates generally to an engine system and, more particularly, to an engine system having a fuel quality sensor.

BACKGROUND

Gaseous fuel powered engines can operate using a range of different fuel mixtures. And some fuel mixtures have a greater heating value and/or lower methane number than other fuel mixtures. If an engine is supplied with fuel having an unexpectedly high methane number ("hot fuel"), damage to the engine can occur. If an engine is supplied with fuel having an unexpectedly low methane number, the engine can perform poorly or not operate at all. Accordingly, it is important to know the methane number of a fuel mixture supplied to a particular engine at a particular time. In some applications, however, the fuel mixture can be variable. This problem may be exacerbated when distributors use a variety of fuel sources to meet demand.

Historically, gaseous fuel powered engines supplied with "hot fuel" were operated in one of two ways. First, an engine could be operated with greater margin at very retarded timings to account for "worst-case" scenarios, such that the engine would be protected from damage regardless of the exact mixture of fuel being supplied to the engine. This mode of operation, however, is generally inefficient, as full advantage of the true heating value in the fuel cannot be taken advantage of. Second, the engine could be operated with less margin until a problem is detected (e.g., until engine knock is detected), and then operation could be adjusted until the problem is no longer detectable. This mode of operation, while more efficient, could also lead to lower engine life, as some damage may have already occurred by the time the problem is detected.

One attempt to address the above-described problems is disclosed in U.S. Pat. No. 5,311,447 (the '447 patent) that issued to Bonne on May 10, 1994. In particular, the '447 patent discloses a combustionless method for measuring the quality of fuel being fed to a gas consumption device. The method includes diverting a portion of the fuel through a sensor chamber, and measuring a viscosity of the fuel at a first sensor in the chamber. The method also includes measuring a thermal conductivity of the fuel with a second sensor in the chamber, at two different temperature levels. The viscosity and thermal conductivity values are then corrected based on a temperature and a pressure of the fuel, and a corresponding heating value is determined using an empirical formula determined as a function of the corrected viscosity and thermal conductivity values. The heating value is then stored, displayed, or given off as a control pulse depending on the information required for a particular application. The empirical formula used to calculate the heating value of the fuel is determined through the use of a commercially available regression analysis program.

Although the method described in the '447 patent may be adequate in some applications, it may be less than optimal. For example, because the method relies on input from two or more different sensors, the associated system may be expensive and complex. In addition, sampling thermal conductivity at only two temperature levels may not provide a desired level of accuracy. Further, by relying on viscosity, temperature, and pressure measurements, the system may be slow. And the speed of the system may preclude its use in highly-transient applications (e.g., in combustion engine applications).

The disclosed engine system is directed to overcoming one or more of the problems set forth above.

SUMMARY

In one aspect, the present disclosure is directed to a fuel quality sensor. The fuel quality sensor may include a single sensing element configured to sense a thermodynamic property of an unknown mixture of gaseous fuel, and a heating element configured to increase a temperature of the unknown mixture of gaseous fuel at the single sensing element to multiple different temperature levels. The fuel quality sensor may also include a microprocessor configured to calculate a fuel parameter of the unknown mixture of gaseous fuel as a function of only the thermodynamic property sensed at the multiple different temperature levels.

In another aspect, the present disclosure is related to a control system for use with an engine. The control system may include a sensing element in fluid communication with a flow of unknown mixture of gaseous fuel supplied to the engine. The sensor may be configured to sense a thermodynamic property of the unknown mixture of gaseous fuel. The control system may also include a heating element configured to increase a temperature of the unknown mixture of gaseous fuel at the sensing element to multiple different temperature levels, and a microprocessor configured to determine a fuel parameter of the unknown mixture of gaseous fuel as a function of the thermodynamic property sensed at the multiple different temperature levels. The control system may also include a controller in communication with the microprocessor and configured to selectively adjust a control parameter of the engine based on the fuel parameter.

In another aspect, the present disclosure is directed to an engine system. The engine system may include an engine having at least one combustion chamber, a fuel delivery system in fluid communication with the at least one combustion chamber, and a supply of gaseous fuel connected to the fuel delivery system. The engine system may also include a sensing element in fluid communication with the supply of gaseous fuel and configured to sense at least one of a heat capacity, a thermal conductivity, and a thermal diffusivity of the gaseous fuel, and a heating element configured to increase a temperature of the gaseous fuel at the sensing element to multiple different temperature levels. The engine system may also include a microprocessor configured to determine at least one of a Lower Heating Value, a Wobbe index, a % Diluents, a Specific Gravity, a Specific Heat Ratio, and a Methane Number as a function of the at least one of the heat capacity and the thermal conductivity sensed at the multiple different temperature levels, and a controller in communication with the microprocessor and the engine. The controller may be configured to selectively adjust at least one of an air/fuel ratio, an engine timing, or a load on the engine based on the at least one of the Lower Heating Value, the Wobbe Index, the % Diluents, the Specific Gravity, the Specific Heat Ratio, and the Methane Number.

In another aspect, the present disclosure is directed to a method of controlling an engine. The method may include sensing a thermodynamic property of an unknown mixture of gaseous fuel as the unknown mixture of gaseous fuel flows into the engine, and heating the unknown mixture of gaseous fuel to multiple different temperature levels as the thermodynamic property of the unknown mixture of gaseous fuel is being sensed. The method may further include determining a fuel parameter of the unknown mixture of gaseous the as a function of the thermodynamic property sensed at the multiple different temperature levels, and selectively adjusting a control parameter of the engine based on the fuel parameter.

DETAILED DESCRIPTION

Figure 1:
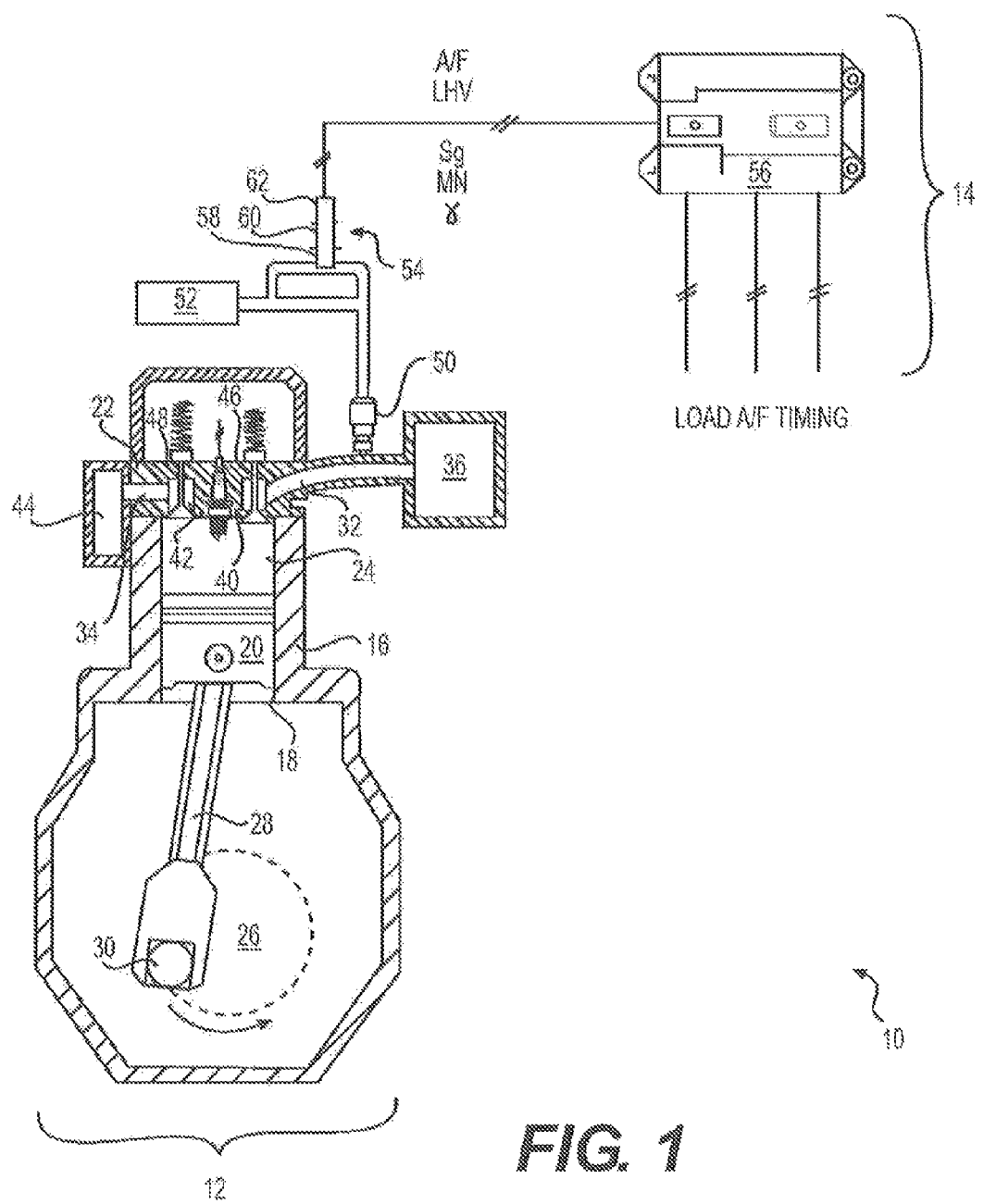
FIG. 1 is a diagrammatic illustration of an exemplary disclosed engine system.
Figure 2:
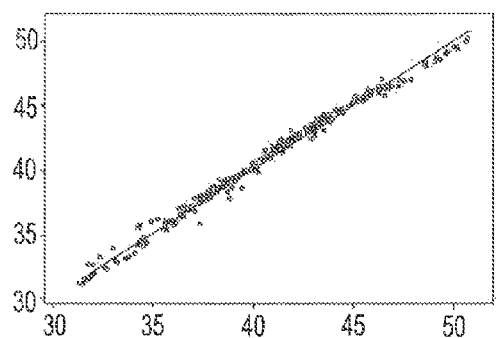
FIGS. 2-11 are graphs depicting exemplary results of executing disclosed methods of engine control.
Figure 3:
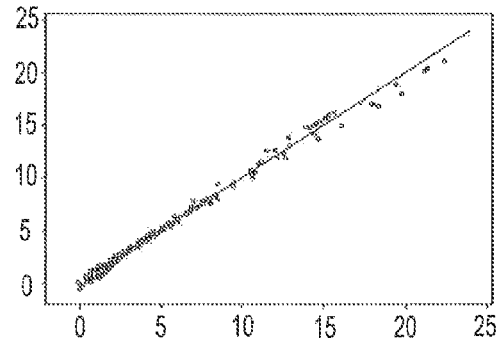
Figure 4:
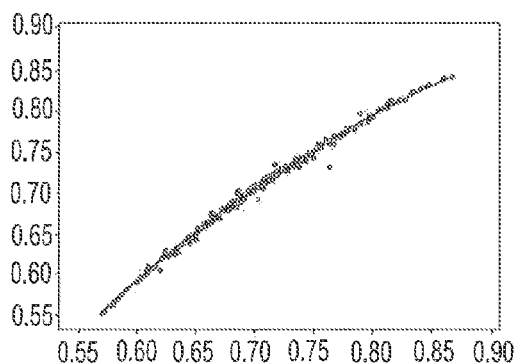
Figure 5:
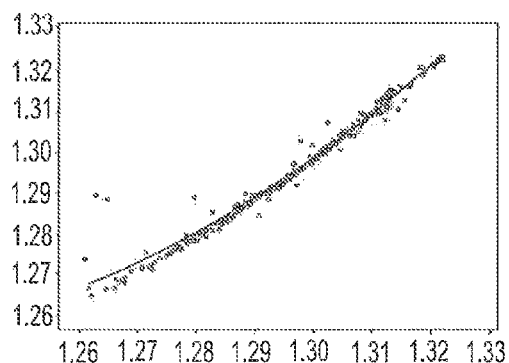
Figure 6:
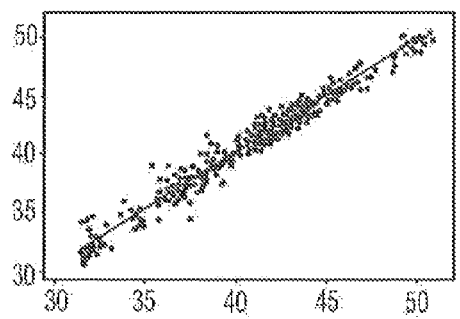
Figure 7:
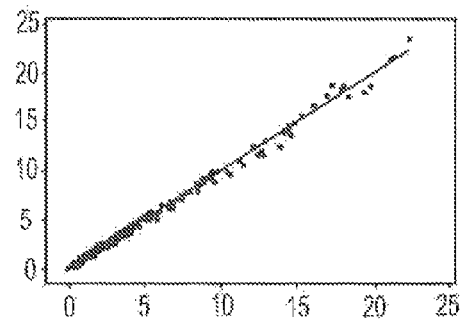
Figure 8:
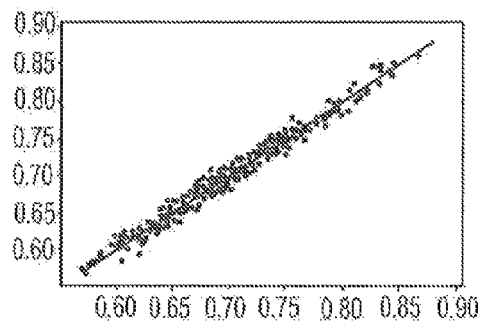
Figure 9:
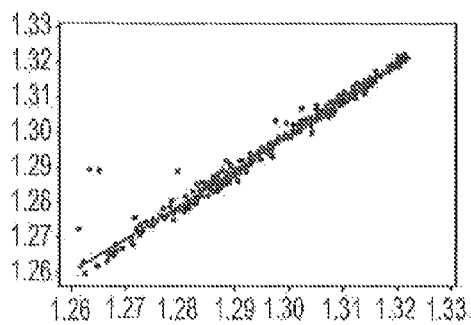
Figure 10:
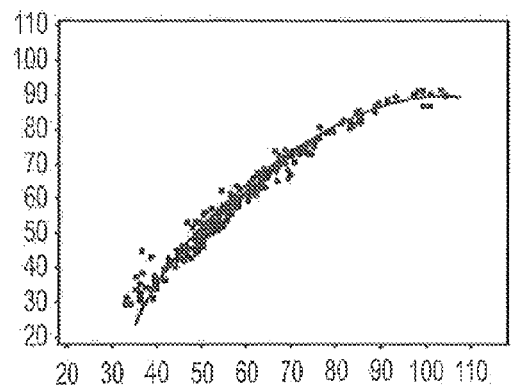

FIG. 1 illustrates an exemplary engine system 10 having an engine 12 and an associated control system 14. For the purposes of this disclosure, engine 12 is depicted and described as a four-stroke gaseous-fueled engine. One skilled in the art will recognize, however, that engine 12 may alternatively be a two-stroke engine, if desired. Engine 12 may include an engine block 16 that at least partially defines one or more cylinders 18 (only one shown in FIG. 1). A piston 20 may be slidably disposed within each cylinder 18 to reciprocate between a top-dead-center (TDC) position and a bottom-dead-center (BDC) position, and a cylinder head 22 may be associated with each cylinder 18. Cylinder 18, piston 20, and cylinder head 22 may together define a combustion chamber 24. It is contemplated that engine 12 may include any number of combustion chambers 24 and that combustion chambers 24 may be disposed in an "in-line" configuration, in a "V" configuration, in an opposing-piston configuration, or in any other suitable configuration.

Engine 12 may also include a crankshaft 26 that is rotatably disposed within engine block 16. A connecting rod 28 may connect each piston 20 to a throw 30 of crankshaft 26 so that a sliding motion of piston 20 between the TDC and BDC positions within each respective cylinder 18 results in a rotation of crankshaft 26. Similarly, a rotation of crankshaft 26 may result in a sliding motion of piston 20 between the TDC and BDC positions. In a four-stroke engine, piston 20 may reciprocate between the TDC and BDC positions through an intake stroke, a compression stroke, a combustion or power stroke, and an exhaust stroke. In a two-stroke engine, a complete cycle may include a compression/exhaust stroke (BDC to TDC) and a power/exhaust/intake stroke (TDC to BDC).

Cylinder head 22 may define an intake passageway 32 and an exhaust passageway 34. Intake passageway 32 may direct compressed air or an air and fuel mixture from an intake manifold 36, through an intake opening 40 and into combustion chamber 24. Exhaust passageway 34 may similarly direct exhaust gases from combustion chamber 24 through an exhaust opening 42 and into an exhaust manifold 44.

An intake valve 46 may be disposed within intake opening 32 and configured to selectively engage a corresponding seat. Intake valve 46 may be movable between a first position, at which intake valve 46 engages the seat and inhibits a flow of fluid relative to intake opening 40, and a second position, at which intake valve 46 is removed from the seat to allow the flow of fluid.

An exhaust valve 48 may be similarly disposed within exhaust opening 42 and configured to selectively engage a corresponding seat. Exhaust valve 48 may be movable between a first position, at which exhaust valve 48 engages the seat to inhibit a flow of fluid relative to exhaust opening 42, and a second position, at which exhaust valve 48 is removed from the seat to allow the flow of fluid.

A series of valve actuation assemblies (not shown) may be operatively associated with engine 12 to move intake and exhaust valves 46, 48 between the first and second positions at desired timings relative to the rotation of crankshaft 26 and/or the position of piston 20. It should be noted that each cylinder head 22 could include multiple intake openings 40 and multiple exhaust openings 42. Each such opening would be associated with either an intake valve 46 or an exhaust valve 48. Engine 12 may include a valve actuation assembly for each cylinder head 22 that is configured to actuate all of the intake valves 46 or all of the exhaust valves 48 of that cylinder head 22. It is also contemplated that a single valve actuation assembly could actuate the intake valves 46 or the exhaust valves 48 associated with multiple cylinder heads 22, if desired. The valve actuation assemblies may each embody, for example, a cam/push-rod/rocker arm arrangement, a solenoid actuator, a hydraulic actuator, and/or any other means for actuating known in the art. It should be noted that the timing at which intake and/or exhaust valves 46, 48 are opened and/or closed may have an effect on engine operation (e.g., an effect on cylinder pressure, temperature, efficiency, detonation timing, etc.), and may be variably controlled in some embodiments.

A fuel delivery system 50 may be associated with engine 12 to direct pressurized fuel from a supply 52 into combustion chamber 24. Fuel delivery system 50 may embody, for example, a valve, a fuel injector, a carburetor, etc. situated in communication with intake passageway 32. It is contemplated that fuel delivery system 50 could be powered electronically, hydraulically, mechanically, and/or pneumatically to pass pressurized fuel directly into combustion chamber 24 or indirectly via intake passageway 32, as desired. The fuel may include a compressed gaseous fuel such as, for example, a mixture of natural gas, propane, bio-gas, landfill gas, hydrogen, and/or another fuel.

The amount of fuel allowed into intake passageway 32 and/or the timing at which the fuel is allowed into intake passageway 32 by fuel delivery system 50 may be associated with a ratio of air-to-fuel (A/F) introduced into combustion chamber 24. Specifically, if it is desired to introduce a lean mixture of air and fuel (i.e., a mixture having a relatively low amount of fuel compared to the amount of air) into combustion chamber 24, fuel delivery system 50 may cause fuel to be directed into passage 32 (and/or combustion chamber 24) for a shorter period of time (or otherwise be controlled to inject less fuel per given cycle) than if a rich mixture of air and fuel (i.e., a mixture having a relatively large amount of fuel compared to the amount of air) is desired. Likewise, if a rich mixture of air and fuel is desired, fuel delivery system 50 may cause fuel to be directed into passage 32 (and/or combustion chamber 24) for a longer period of time (or otherwise be controlled to inject more fuel per given cycle) than if a lean mixture is desired.

Control system 14 may include components that cooperate to regulate operations of engine 12 (e.g., intake valve 46, exhaust valve 48, fuel delivery system 50, a load driven by engine 12, etc.) in response to various sensed parameters and/or input. The components may include, among other things, a fuel quality sensor 54 and a controller 56. Fuel quality sensor 54 may be configured to determine one or more quality parameters associated with the fuel being consumed by engine 12 and direct corresponding signals to controller 56 indicative of values of the parameters. Controller 56 may be configured to selectively adjust engine operations in response to the value of the fuel quality parameter.

Fuel quality sensor 54 may be an assembly of multiple components, including, for example, a sensing element 58, a heating element 60, and a microprocessor 62. In one embodiment, sensing element 58 may include one or more electrodes (e.g., a sensing electrode positioned spatially near heating element 60, and a reference electrode spaced away from heating element 60). A current may be passed through the electrode(s), a resistance to the current measured, and the resistance correlated to a particular thermodynamic property of gaseous fuel in the vicinity of the electrode(s). In the disclosed embodiment, the thermodynamic property may include a heat capacity, a thermal conductivity, and/or a thermal diffusivity of the gaseous fuel. It is contemplated that any type of sensing element 58 may be used for this purpose.

Fuel quality sensor 54 may be situated within a main fuel delivery passage or within a bypass, as desired. The flow of fuel past and/or through fuel quality sensor 54 may be held substantially continuous or stagnant during sensing of the thermodynamic property. This flow of fuel may be controlled in any conventional manner known in the art (e.g., via controlled movement of upstream and/or downstream valves—not shown).

The thermodynamic property may be a property that varies based on temperature, and varies differently for different gaseous fuels. Accordingly, heating element 60 may be used to heat the gaseous fuel at sensing element 58 (i.e., in the general vicinity of sensing element 58) to multiple different temperature levels for use in determining how the property varies for the particular unknown mixture of gaseous fuel currently being fed into engine 12. In the disclosed embodiment, heating element 60 may be configured to heat the unknown mixture of gaseous fuel to fourteen different temperature levels as sensing element 58 is sensing the thermodynamic property. It is contemplated, however, that as many different temperature levels may generated, as desired.

Microprocessor 62 may be configured to receive the signal generated by sensing element 58 at the different temperature levels, and calculate one or more particular fuel quality parameters based on the signal. In the disclosed embodiment, the fuel quality parameters include an Air-to-Fuel Ratio (A/F), a Lower Heating Value (LHV), a Wobbe index (WI), a Specific Gravity (Sg), a Methane Number (MN), and a Specific Heat Ratio (γ). Microprocessor 62 may calculate the fuel quality parameter(s) using one or more empirical formulas stored in memory. For example, to calculate the Methane Number for a particular unknown mixture of gaseous fuel being fed into intake passageway 32 by injector 50, microprocessor 62 may insert values for the thermodynamic properties at the different temperature levels into the following equation:

$$MN = C_0 + \sum_i^a C_j C_{pj}$$

wherein:
$C_{pi}$ is heat capacity for the unknown mixture of gaseous fuel at each different temperature level; and
$C_0$ and $C_j$ are multivariate regression constants of known gaseous fuels anticipated to be consumed by engine 12.

As can be seen in FIGS. 2-5, calculation of values for LHV, % Diluents, Sg, and γ, respectively, by microprocessor 62 based on heat capacity sensed by sensing element 58 has proven to be successful. Specifically, hundreds of different fuel mixtures were directed in one simulation or numerical experiment from supply 52 toward injector 50 and past sensor 54. And sensor 54 was used to determine values for LHV, % Diluents, Sg, and γ. These values (Y-axis) were then compared to known values (X-axis) for the same fuels, and the graphs shown in FIGS. 2-5 illustrate the results of this comparison. As can be seen in these graphs, the standard deviation and error for each comparison is relatively low for each fuel quality parameter when calculated as a function of measured heat capacity.

Figure 11:
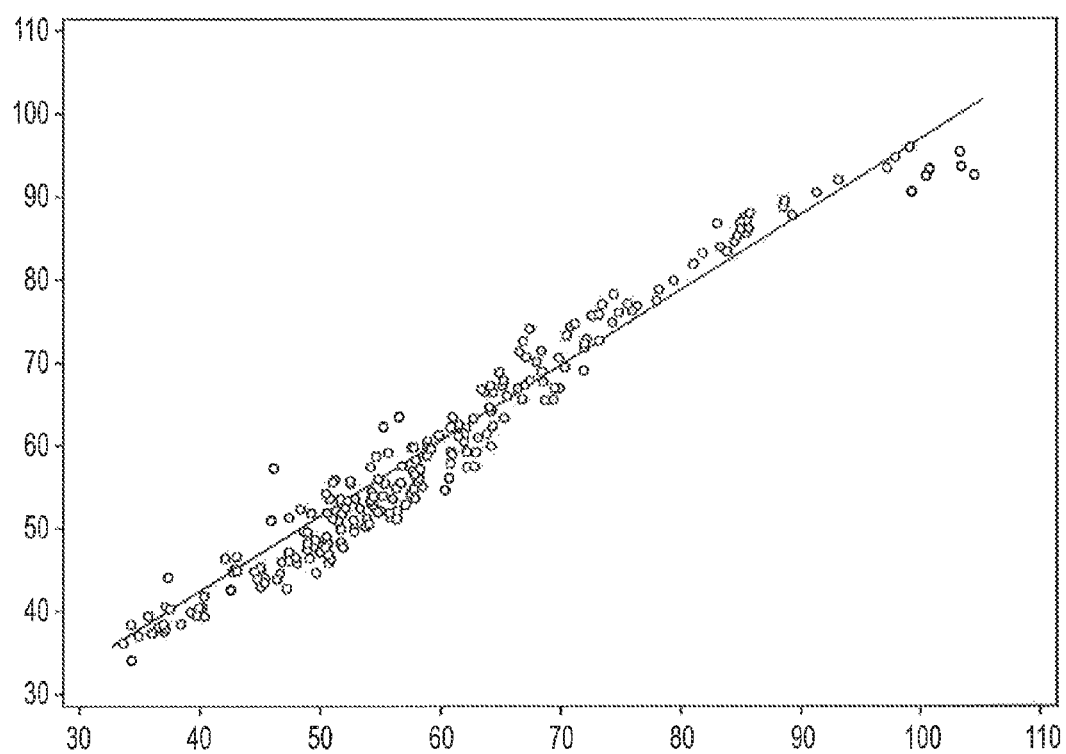
Figure 12:
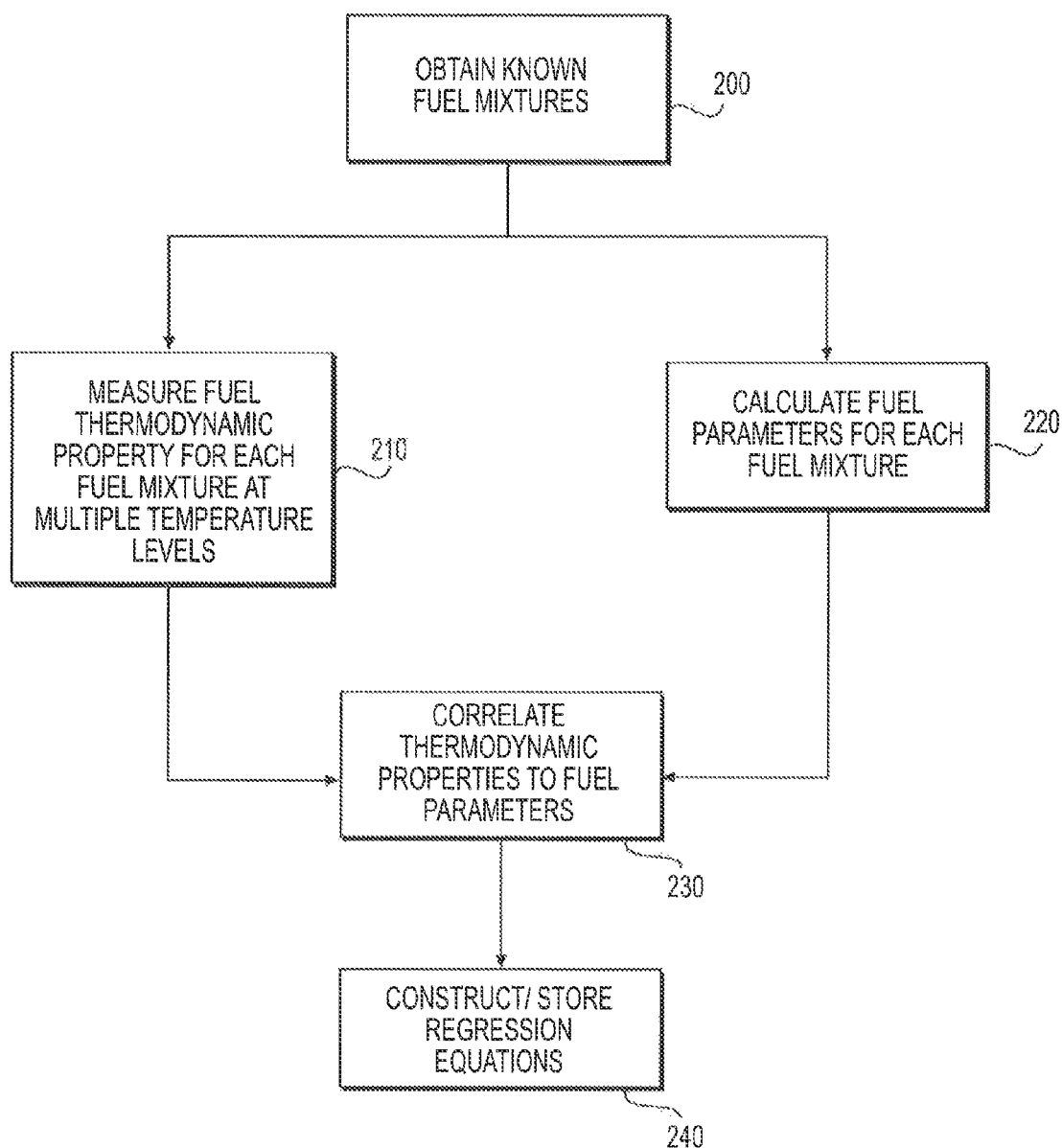
FIGS. 12 and 13 are flowcharts depicting exemplary disclosed methods that may be performed by the engine system of FIG. 1.

Similarly, FIGS. 6-10 show that values (Y-axis) for LHV, % Diluents, Sg, γ, and MN, respectively, of known gaseous fuels calculated using the empirical equations stored within microprocessor 62 and based on thermal conductivity values generated by sensing element 58 compare closely with established values (X-axis) for these same fuels. FIG. 11 shows that values (Y-axis) for MN of known gaseous fuels calculated using the empirical equations stored within microprocessor 62 and thermal diffusivity values, as generated by sensing element 58, compare closely with established values (X-axis) for these same fuels. A method of generating the empirical equations used by microprocessor 62 to determine the thermodynamic properties of unknown mixtures of gaseous fuels is illustrated in FIG. 12, which will be described in more detail below.

Controller 56 may embody a single processor or multiple processors that include a means for controlling an operation of engine system 10. Numerous commercially available processors may perform the functions of controller 56. Controller 56 may include or be associated with a memory for storing data such as, for example, an operating condition, design limits, performance characteristics or specifications of engine system 10, operational instructions, and corresponding fuel quality parameters. Various other known circuits may be associated with controller 56, including power supply circuitry, signal-conditioning circuitry, solenoid driver circuitry, communication circuitry, and other appropriate circuitry. Moreover, controller 56 may be capable of communicating with other components of engine system 10 (e.g., with the valve actuation assemblies, fuel delivery system 50, the load driven by engine 12, etc.) via either wired or wireless transmission and, as such, controller 56 may be connected to or alternatively disposed in a location remote from engine 12.

Controller 56 may be configured to selectively adjust operation of engine 12 based on the fuel quality parameters calculated by microprocessor 62. For example, controller 56 may be capable of causing intake and/or exhaust valves 46, 48 to open earlier relative to the movement of piston 20 (referring to FIG. 1), to stay open longer, and/or to open by a different lift amount. This change in valve timing may have an effect on an amount of air and/or fuel allowed into combustion chamber 24, and a resulting pressure, temperature, efficiency, and/or emissions. Likewise, controller 56 may be capable of causing fuel delivery system 50 to deliver more or less fuel at any desired timing into passage 32 (and/or into combustion chamber 24) to thereby change an air-to-fuel ratio of engine 12 and affect a resulting speed output, power output, efficiency, emissions, etc. Controller 56 could also be capable of changing a load on engine 12, for example increasing or decreasing the load. It is contemplated that controller 56 could affect engine operation in other ways as well.

Figure 13:
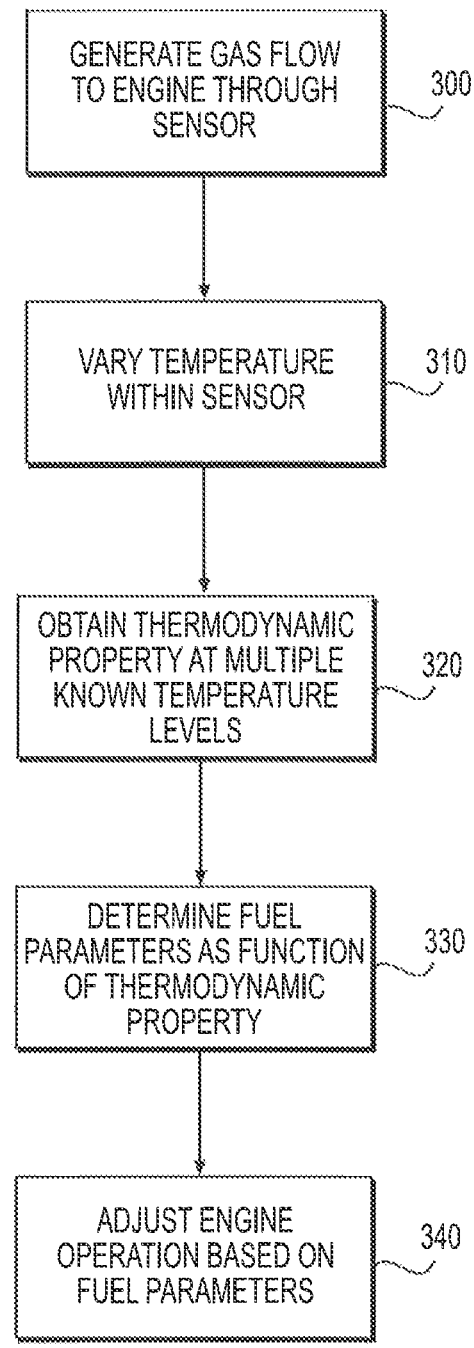

Controller 56 may adjust engine operation based on the fuel quality parameters to improve operation under a given set of conditions. That is, based on the fuel quality parameters, controller 56 may need to change engine operation so as to avoid damaging situations (e.g., engine knock, over pressure, over temperature, etc.), improve efficiency and/or power output, and/or to accomplish other user-specified goals. FIG. 13 shows a flowchart depicting the method of controlling engine 12 based on the calculated fuel quality parameters. FIG. 13 will be discussed in more detail in the following section to further illustrate the disclosed concepts.

INDUSTRIAL APPLICABILITY

The disclosed engine system may be applicable to situations of changing fuel supply, where continued operation of the associated engine at high levels of performance is desired. The disclosed engine system may help ensure continued operation by selectively implementing engine-protecting adjustments based on changing fuel quality parameters that are detected by the system. The disclosed engine system may also help ensure high-level engine performance by selectively implementing engine adjustments that take full advantage of the energy contained within the changing fuel supply. Operation of engine system 10 will now be described with respect to FIGS. 12 and 13.

Before microprocessor 62 can generate the fuel parameters used by controller 56 to adjust engine operation, the empirical formulas used by microprocessor 62 must first be determined. The flowchart of FIG. 12 illustrates this process. As shown in FIG. 12, the first step may include obtaining multiple different fuel mixtures that are anticipated to be used by engine 12 (Step 200). For each of the different fuel mixtures, desired thermodynamic properties may then be measured at multiple different temperature levels (Step 210). Step 210 may be performed in a controlled environment (e.g., in a lab), and the number of different temperature levels may correlate with the number of different temperature levels at which sensor 54 is intended to operate. As disclosed above, these thermodynamic properties can include, among others, any one or more of heat capacity, thermal conductivity, and thermal diffusivity.

Fuel quality parameters of these same known fuel mixtures may be calculated and/or measured at about the same time as completion of step 210 (Step 220). As described above, these fuel quality parameters may include, among others, any one or more of A/F, LHV, WI, Sg, MN, and $\gamma$. At step 220, the calculating and/or measuring of the fuel quality parameters may be completed in any manner known in the art. The thermodynamic properties measured in step 210 may then be correlated with the fuel properties determined in step 220 (Step 230). This correlation may be done in any way known in the art. In the disclosed embodiment, the correlation is done through multivariate regression analysis using a commercially available software program, and the empirical equation described above may be one exemplary result of the correlation. The empirical equations may then be stored within the memory of microprocessor 62 for use during operation of engine system 10 (Step 240).

Once microprocessor 62 has been programmed with the necessary empirical equations, engine system 10 may follow the process of FIG. 13. Specifically, a flow of gaseous fuel may be directed from supply 52 through injector 50 and into passageway 32 (Step 300). In many situations, the identification of the exact mixture of gaseous fuel may be unknown and may change throughout operation of engine 12.

As the flow of gaseous fuel passes into (e.g., passes continuously through or is stagnant in the general vicinity of) sensor 54, heating element 60 may be caused by microprocessor 62 to vary the temperature of the gaseous fuel (Step 310). As described above, heating element 60 may be configured to vary the temperature to multiple different and discrete temperature levels, for example to 3 or more (e.g., 7) different temperature levels. At each temperature level, sensing element 58 may be caused to obtain one or more thermodynamic properties of the unknown gaseous fuel mixture (Step 320). Sensing element 58 may venerate signals indicative of these properties and direct the signals to microprocessor 62. The flow may be held continuous or intermittently direct into/past fuel quality sensor 54 and then selectively stagnated during sensing using any means known in the art.

Upon receiving the signals from sensing element 58, microprocessor 62 may use the empirical formulas stored in memory to determine the fuel quality parameters as functions of the thermodynamic properties (Step 330). Microprocessor 62 may then generate signals indicative of the fuel properties and direct these signals to controller 56. In most situations, the fuel quality parameters communicated by microprocessor 62 to controller 56 may not include an indication of the exact mixture of gaseous fuel being consumed by engine 12. Although it may be possible that additional correlations can be contrasted to help predict the composition of the gaseous fuel mixture, if desired. Controller 56 may then use the fuel quality parameter information to adjust and regulate engine operation in the manner described above (Step 340).

The disclosed engine system may provide several benefits. First, the disclosed engine system may be relatively simple, having only a single sensor. This simplicity may help to reduce a cost of engine system 10. In addition, by sampling thermodynamic properties at many different levels, an accuracy of the measurement may be increased. Further, because only a single thermodynamic property is required to determine a corresponding fuel quality parameter, the system may be responsive, allowing for wide application in transient systems.

It will be apparent to those skilled in the art that various modifications and variations can be made to the engine system of the present disclosure. Other embodiments of the engine system will be apparent to those skilled in the art from consideration of the specification and practice disclosed herein. It is intended that the specification and examples be considered as exemplary only, with a true scope of the disclosure being indicated by the following claims and their equivalents.

What is claimed is:

1. A fuel quality monitoring sensor, comprising:
   a single sensing element configured to sense a thermodynamic property of an unknown mixture of gaseous fuel;
   a heating element configured to increase a temperature of the unknown mixture of gaseous fuel at the single sensing element to multiple different temperature levels; and
   a microprocessor configured to calculate a fuel parameter of the unknown mixture of gaseous fuel as a function of only the thermodynamic property sensed at the multiple different temperature levels and no other sensed property.

2. The fuel quality monitoring sensor of claim 1, wherein the thermodynamic property is one of a heat capacity and a thermal conductivity of the unknown mixture of gaseous fuel.

3. The fuel quality monitoring sensor of claim 1, wherein the fuel parameter is one of a Lower Heating Value, a Wobbe index, a % Diluents, a Specific Gravity, a Specific Heat Ratio, and a Methane Number.

4. The fuel quality monitoring sensor of claim 1, wherein the microprocessor is configured to calculate the fuel parameter using an empirical formula determined through multivariate regression analysis performed on measured thermodynamic properties and measured fuel parameters of known mixtures of fuels anticipated to be sensed by the single sensing element.

5. A control system for use with an engine, comprising:
a sensing element in fluid communication with a flow of unknown mixture of gaseous fuel supplied to the engine, the sensing element configured to sense a thermodynamic property of the unknown mixture of gaseous fuel;
a heating element configured to increase a temperature of the unknown mixture of gaseous fuel at the sensing element to multiple different temperature levels;
a microprocessor configured to determine a fuel parameter of the unknown mixture of gaseous fuel as a function of only the thermodynamic property sensed at the multiple different temperature levels and no other sensed property; and
a controller in communication with the microprocessor and configured to selectively adjust a control parameter of the engine based on the fuel parameter.

6. The control system of claim 5, wherein:
the sensing element is the only sensing element providing information to the microprocessor; and
the microprocessor is configured to determine the fuel parameter of the unknown mixture of gaseous fuel as a function of only the thermodynamic property.

7. The control system of claim 5, wherein the thermodynamic property is a heat capacity of the unknown mixture of gaseous fuel.

8. The control system of claim 5, wherein the thermodynamic property is one of a thermal conductivity and a thermal diffusivity of the unknown mixture of gaseous fuel.

9. The control system of claim 5, wherein the fuel parameter is a Lower Heating Value.

10. The control system of claim 5, wherein the fuel parameter is one of a Wobbe index and a % Diluents.

11. The control system of claim 5, wherein the fuel parameter is a Specific Gravity.

12. The control system of claim 5, wherein the fuel parameter is a Specific Heat Ratio.

13. The control system of claim 5, wherein the fuel parameter is a Methane Number.

14. The control system of claim 5, wherein the microprocessor is configured to calculate the fuel parameter using an empirical formula determined through multivariate regression analysis performed on measured thermodynamic properties and measured fuel parameters of known fuels anticipated to be sensed by the sensing element.

15. The control system of claim 5, wherein the control parameter is one of an air/fuel ratio, an engine timing, or a load on the engine.

16. An engine system, comprising:
an engine having at least one combustion chamber;
a fuel delivery system in fluid communication with the at least one combustion chamber;
a supply of gaseous fuel connected to the fuel delivery system;
a sensing element in fluid communication with the supply of gaseous fuel and configured to sense at least one of a heat capacity and a thermal conductivity of the gaseous fuel;
a heating element configured to increase a temperature of the gaseous fuel at the sensing element to multiple different temperature levels;
a microprocessor configured to determine at least one of a Lower Heating Value, a Wobbe index, a % Diluents, a Specific Gravity, a Specific Heat Ratio, and a Methane Number as a function of the at least one of the heat capacity and thermal conductivity sensed at the multiple different temperature levels; and
a controller in communication with the microprocessor and the engine, the controller being configured to selectively adjust at least one of an air/fuel ratio, an engine timing, or a load on the engine based on the at least one of the Lower Heating Value, the Wobbe index, the % Diluents, the Specific Gravity, the Specific Heat Ratio, and the Methane Number, and no other sensed property.

17. A method of monitoring a quality of an unknown mixture of gaseous fuel supplied to an engine, comprising:
sensing a thermodynamic property of the unknown mixture of gaseous fuel as the unknown mixture of gaseous fuel flows into the engine;
heating the unknown mixture of gaseous fuel to multiple different temperature levels as the thermodynamic property of the unknown mixture of gaseous fuel is being sensed;
determining a fuel parameter of the unknown mixture of gaseous fuel as a function of only the thermodynamic property sensed at the multiple different temperature levels and no other sensed property; and
selectively adjusting a control parameter of the engine based on the fuel parameter.

18. The method of claim 17, wherein the thermodynamic property is one of a heat capacity and a thermal conductivity of the unknown mixture of gaseous fuel.

19. The method of claim 17, wherein the fuel parameter is one of a Lower Heating Value, a Wobbe index, a % Diluents, a Specific Gravity, a Specific Heat Ratio, and a Methane Number.

20. The method of claim 17, wherein the control parameter is one of an air/fuel ratio, an engine timing, or a load on the engine.

* * * * *